United States Patent [19]

Kinder et al.

[11] Patent Number: 5,106,948

[45] Date of Patent: Apr. 21, 1992

[54] CYTOTOXIC BORONIC ACID PEPTIDE ANALOGS

[75] Inventors: David H. Kinder, Pullman, Wash.; Matthew M. Ames, Rochester, Minn.

[73] Assignee: Mao Foundation for Medical Education and Research, Rochester, Minn.

[21] Appl. No.: 574,294

[22] Filed: Aug. 28, 1990

Related U.S. Application Data

[63] Continuation-in-part of Ser. No. 199,891, May 27, 1988, Pat. No. 4,963,655.

[51] Int. Cl.$^5$ .......................... C07K 5/00; C07K 7/00; A61K 37/00; A01N 55/08
[52] U.S. Cl. ..................................... 530/331; 530/402
[58] Field of Search ................... 514/64, 18, 19; 530/331, 402

[56] References Cited

U.S. PATENT DOCUMENTS 4,499,082 2/1985 Shenvi et al. ........................ 514/2
4,537,773 8/1985 Shenvi ................................ 514/63

OTHER PUBLICATIONS

Peptide Hormones, Parsons, Ed., "Characteristics of the Amino Acid as Components of a Peptide . . . ", pp. 1-6 (1976).
D. H. Kinder et al., *J. Med. Chem.*, 28, (1985).
B. Goz et al., *Biochem. Pharmacol.*, 35, 3587 (1986).
D. S. Matteson et al., *J. Amer. Chem. Soc.*, 103, 5241 (1981).
C. A. Kettner and A. B. Shenvi, *J. Biol. Chem.*, 259, 15106 (1984).

*Primary Examiner*—Lester L. Lee
*Assistant Examiner*—E. J. Kraus
*Attorney, Agent, or Firm*—Merchant, Gould, Smith, Edell, Welter & Schmidt

[57] ABSTRACT

A method is provided for inhibiting growth of cancer cells comprising contacting said cells with an effective growth-inhibiting amount of a compound of the formula (II):

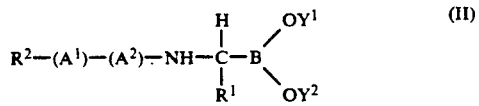

or a physiologically acceptable salt thereof, wherein $A^1$ and $A^2$ are individually L-amino acid residues selected from the group consisting of Ala, Pro, Gly, Glu, Leu, Lys, Phe, Ser, Val, Ile, Arg, Tyr, Thr, Asp, Asn and Gly; $R^1$ is $C_1-C_6$(alkyl) which is unsubstituted or is substituted with an aromatic substituent or one or more in-chain bivalent groups selected from the group consisting of —O—, —CO—, —S—, —NH—, —CONH—, CH=CH—, and —SO$_2$—; $Y^1$ and $Y^2$ are each H, or taken together from a moiety derived from a dihydroxy compound, and $R^1$ is H or an N-terminal protecting group.

10 Claims, 6 Drawing Sheets

Cbz-Ala-l-boroValine

Cbz-Ala-l-boroPhenylalanine

Substrate Hydrolysis

Boronic Acid Binding

CYTOTOXIC BORONIC ACID PEPTIDE ANALOGS

BACKGROUND OF THE INVENTION

This invention was made with government support under grant CA 09441 awarded by the National Cancer Institute. The Government of the United States has certain rights in this invention.

CROSS-REFERENCE TO RELATED APPLICATION

This application is a continuation-in-part of U S. patent application Ser. No. 199,891, filed May 27, 1988 now U.S. Pat. No. 4,963,655.

FIELD OF THE INVENTION

This invention relates to boron analogs of amino acids and small peptides and the use of the analogs to inhibit growth or colony formation of mammalian cells. More specifically, the present invention relates to methods to prepare boronic acid analogs of tripeptides or dipeptides, and their use to inhibit tumor growth in vivo and in vitro.

Three major families of antitumor agents are known. Each of the families of agents is associated with a recognized mechanism of action. First, antitumor agents may be alkylating agents, which generally bind in a covalent manner with DNA to form bifunctional lesions. The bifunctional lesions involve adjacent or nearby bases on the same strand, or alternatively, involve bases on opposite strands forming interstrand crosslinks. Second, antitumor agents may be antimetabolites, which generally inhibit enzymes involved in the synthesis or assembly of DNA. Alternatively, an antimetabolite may serve as a fraudulent or analog substrate of DNA processes. Third, antitumor agents may be antibiotics, which work by intercalating into the DNA helix or introducing strand breaks into DNA.

Thousands of potential anticancer agents have been evaluated. Essentially, all effective agents (of which very few have been found) appear to work by one of the above-mentioned mechanisms. The subject invention concerns a class of molecules which are not associated with any of the three major families of antitumor agents.

Proteases are ubiquitous enzymes involved in a myriad of cellular activities including digestion, blood coagulation and fibrinolysis, the processing and degradation of proteins, sperm penetration, and have been implicated as important components in regulating cascades.

Proteases and protease inhibitors have been reported in association with cancer-related processes. The most common associations involve increased protease enzyme activities or enzyme concentration. Such increased protease activity may be associated with transformation of cells by viruses, chemicals or other agents, as well as with the metastatic potential of cancer cells. Additionally, data have been published which suggest that protease inhibitors may prevent or reduce the incidence of transformation and reduce the metastatic potential of cancer cells. A number of protease inhibitors has been previously evaluated against murine tumor cells in both culture and in whole animals as potential antitumor agents. Reports exist of modest growth inhibition of cells in culture following exposure to protease inhibitors, such as chloromethyl ketones, soybean trypsin inhibitor, ovomucoid, and aprotinin. Most are inert or require very high concentrations to achieve significant tumor cell killing.

The synthesis and protease inhibition properties of a number of dipeptide analogs, including Cbz-ala-1-borovaline and Cbz-ala-1-borophenylalanine, wherein Cbz is an abbreviation for the benzyloxycarbonyl protecting group, and Ala is the abbreviation for the alanyl peptidyl residue, have been previously reported (D. H. Kinder et al., *J. Med. Chem.*, 28, 1917 (1985)). The structures of these two analogs are depicted in FIG. 1. One of the analogs, Cbz-ala-1-borophenylalanine, has also been evaluated for its ability to inhibit cultured human nasopharyngeal carcinoma cells and Lewis lung murine tumor cells (Goz et al., *Biochem. Pharmacol.*, 35, 3587 (1986)).

The synthetic route employed by D. H. Kinder et al. was based on the route disclosed by D. Matteson et al., *J. Amera. Chem. Soc.*, 103, 5241 (1981) for the synthesis of (R)-1-acetamido-2-phenylethaneboronic acid. The synthetic route can be summarized as shown in Scheme 1, hereinbelow:

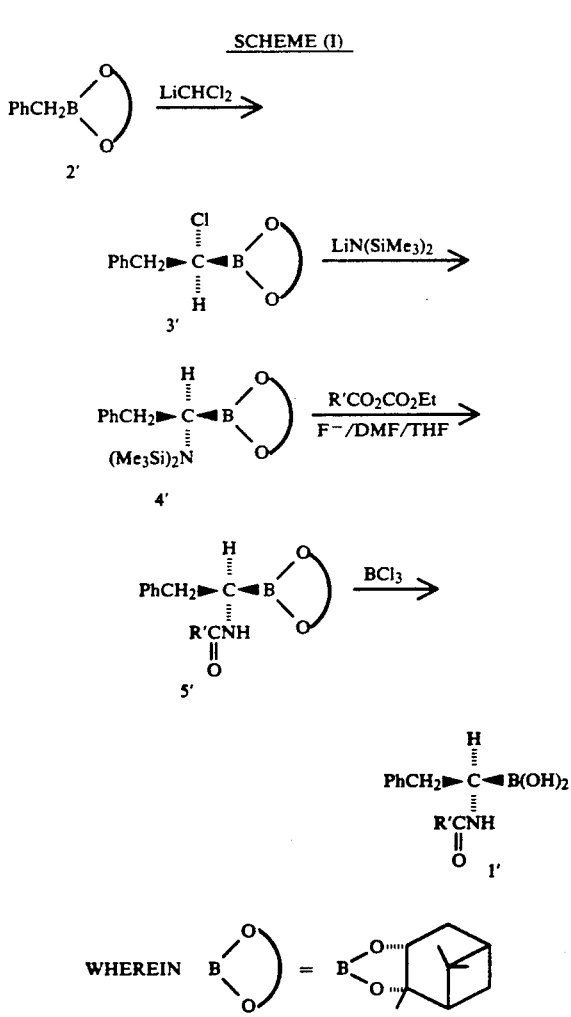

When, for example, $R^1$ is Cbz-ala, compound 1' is Cbz-ala-1-borophenylalanine.

A. B. Shenvi et al. (U.S. Pat. No. 4,499,082) discloses tri- and tetrapeptide analogs of the general formula:

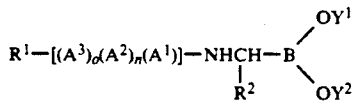

wherein $A^1$, $A^2$ and $A^3$ are amino acid residues, n is 1 and o is 0 or 1, $Y^1$ and $Y^2$ are each H, or represent a divalent protecting group, $R^2$ is, e.g., alkyl or aralkyl and $R^1$ is H or an N-terminal protecting group such as Cbz. Specific tripeptide analogs are the subject of Examples 11, 16–19 and 22 of this patent. These α-aminoboronic acid peptides are disclosed to be useful as inhibitors of metallo, acid, and serine proteases. Suggested therapeutic uses for these compounds include the treatment of emphysema. A. B. Shenvi (U.S. Pat. No. 4,537,773) generally discloses and claims compounds of formulas 2 and 3 as depicted in Scheme I, hereinabove, e.g., wherein the benzyl substituent has been replaced by lower alkyl.

However, a need exists for new synthetic routes to boronic acid peptides. A further need exists for new therapeutic uses of boronic acid peptides.

SUMMARY OF THE INVENTION

The present invention provides a therapeutic method to inhibit the replication of cancer cells in vivo or in vitro by contacting said cancer cells with an effective amount of certain α-aminoboronic acid peptides. For example, the growth of cancer cells such as sarcoma, melanoma, leukemia or carcinoma cells can be inhibited in accord with the present method. More specifically, the present invention provides a method comprising the administration of an amount of certain dipeptidylaminoalkylboronic acids to a mammal, such as a human patient, afflicted with a cancer, in an amount effective to cure or ameliorate said cancer, or the symptoms associated therewith. The dipeptidylaminoalkylboronic acids, or "tripeptide analogs," which are useful in the practice of the present invention, are of the general formula (I):

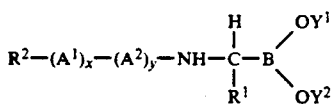

or a physiologically acceptable salt thereof, wherein $x=y=1$, $A^1$ and $A^2$ are individually L-amino acid residues selected from the group consisting of Ala, Pro, Gly, Glu, Leu, Lys, Phe, Ser, Val, Ile, Arg, Tyr, Thr, Asp, Asn and Gly; $R^1$ is $C_1$–$C_6$(alkyl) which is unsubstituted or is substituted with an aromatic substituent or one or more in-chain bivalent groups selected from the group consisting of —O—, —CO—, —S—, —NH—, —CONH—, —CH=CH—and —SO$_2$—; $Y^1$ and $Y^2$ are each H, or taken together form a moiety derived from a dihydroxy compound having at least two hydroxy groups separated by at least two connecting atoms in a chain or ring, said chain or ring comprising carbon atoms, and optionally, a heteroatom or heteroatoms which can be N, S or O; with the proviso that when the heteroatom is O, $R^2$ cannot be H; and $R^2$ is H or an N-terminal protecting group. Preferably, $Y^1=Y^2=$H, $R^1$ is benzyl, methyl, isopropyl, 2-butyl, or isobutyl; most preferably, $R^1$ is benzyl or ($C_1$–$C_3$)alkyl, A is Ala, $A^2$ is Ala, Pro, Gly or Val and $R^2$ is an N-terminal protecting group such as Cbz or 7-methoxycoumarin-4-ylacetyl.

The present invention also provides a general method for the synthesis of compounds of the formula I, and of dipeptide analogs of formula I wherein $x=o$ and $y=1$. The synthesis of dipeptide analogs of formula I in accord with this route is depicted in FIG. 6. The synthesis of the tripeptide analog of formula 10 in accord with this route is depicted in FIG. 7. More generally, the present method comprises the steps of:

(a) converting a protected amino acid of the formula: $R^2$—($A^1$)—OH(15) into a compound of the formula $R^2$—($A^1$)—N$_3$(18), wherein $A^1$ is as defined hereinabove and $R^2$ is an N-terminal protecting group, so that the amido group (N$_3$) replaces the OH present on the CO$_2$H group of amino acid ($A^1$)OH;

(b) reacting the compound of the formula $R^2$-($A^1$)-N$_3$(18) with (i) a compound of the formula:

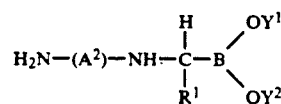

wherein $A^2$ and $R^1$ are as defined hereinabove and wherein $Y^1$ and $Y^2$ taken together form a moiety derived from a dihydroxy compound as defined above to yield a compound of the formula (20):

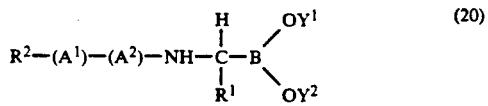

wherein $Y^1$, $Y^2$, $R^2$, $A^1$, $A^2$ and $R^1$ are as defined hereinabove for compounds 18 and 19; or, reacting compound (18) with (ii) a compound of the formula:

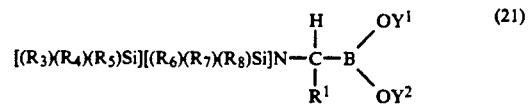

wherein $Y^1$ and $Y^2$ are as defined above for compound 9, and $R_3$, $R_4$, $R_5$, $R_6$, $R_7$ and $R_8$ are individually ($C_1$–$C_4$)alkyl, to yield a compound of the formula:

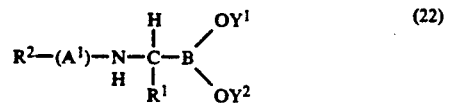

wherein $R^2$, $A^1$, $R^1$, $Y^1$ and $Y^2$ are as defined hereinabove for compounds 18 and 19. Optionally, compounds 20 or 22 can be converted into the corresponding boronic acids ($Y^1=Y^2=$H) by, e.g., cleavage of the boronate ester with BCl$_3$, and/or can be converted into the free polypeptide ($R^2=$H) by removal of the N-terminal protecting group, e.g., by hydrogenolysis.

Preferably, the amino acid acyl azide (18) is generated in a solvent system including [bis(isopropyl)]-ethylamine (i-Pro$_2$NEt), THF and DMF, by means of a reagent such as diphenylphosphoryl azide ((PhO)$_2$-

P(O)N₃), followed by treatment with tetrabutylammonium fluoride-dihydrofluoride (n-Bu₄NF.2HF).

As given herein, the abbreviations for the L-amino acid residues are in accord with art-recognized nomenclature for peptidyl residues, as set forth in Shenvi et al., (U.S. Pat. No. 4,499,082) at Col. 4, line 53, through Col. 5, line 8, the disclosure of which is incorporated by reference herein.

DETAILED DESCRIPTION OF THE INVENTION

Figure 1:
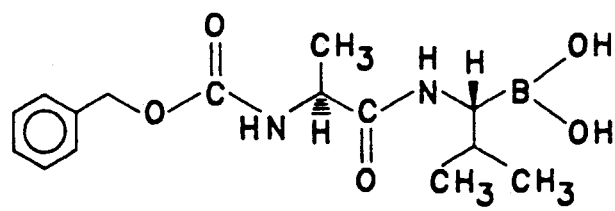
FIG. 1 illustrates the structure of the protease inhibitors Cbz-ala-1-borovaline and Cbz-ala-1-borophenylalanine. Synthesis and apparent $K_1$ values are from Kinder and Katzenellenbogen, *J. Med. Chem.*, 28, 1917 (1985).
Figure 1:
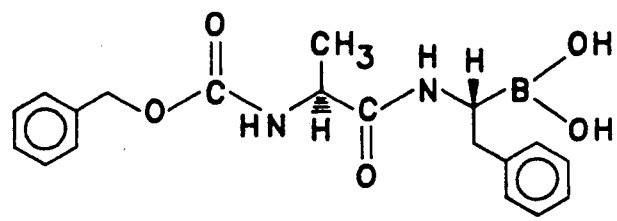

The synthetic method of the present invention is summarized below in Scheme II:

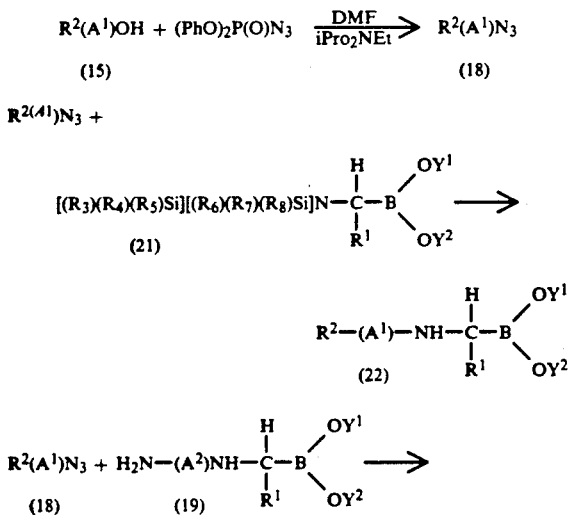

-continued
SCHEME (II)

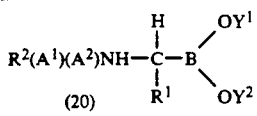

wherein A¹ and A² are individually L-amino acid residues selected from the group consisting of Ala, Pro, Gly, Glu, Leu, Lys, Phe, Ser, Val, Ile, Arg, Tyr, Thr, Asp, Asn and Gly; R¹ is $C_{1-6}$(alkyl) which is unsubstituted or is substituted with an aromatic substituent or one or more in-chain bivalent groups selected from the group consisting of —O—, —CO—, —S—, —NH—, —CONH—, —CH=CH—and —SO₂—; Y¹ and Y² taken together form a moiety derived from a dihydroxy group having at least two hydroxy groups separated by at least two connecting atoms in a chain or ring comprising carbon atoms, and optionally, a heteroatom or heteroatoms which can be N, S or O; with the proviso that when the heteroatom is O, R² cannot be H; and R² is an N-terminal protecting group, and R₃, R₄, R₅, R₆, R₇, and R₈ are individually $C_{1-4}$(alkyl).

Therefore, compound 15 is an N-protected amino acid wherein the carboxylic acid moiety is converted into an azidocarbonyl group by reaction with diphenylphosphoryl azide. Compound 18 is reacted in situ with 1-(bistrialkylsilyl)aminoboronic ester (21) in the presence of tetrabutyl ammonium fluoride-dihydrofluoride in DMF/THF to yield the N-protected boronic ester (22) which is referred to as a "dipeptide analog." The synthesis of compound (18) is fully set forth in Shenvi et al. (U.S. Pat. No. 4,537,773), the disclosure of which is incorporated by reference herein.

Alternatively, the N-protecting group of compound (22) can be removed, e.g., by hydrogenolysis, to yield a compound (19) which can be reacted with compound 18 in the presence of THF/DMF to yield protected tripeptide analog 20. The boronate ester can be cleaved in BCl₃/CH₂Cl₂ to yield the boronic acid, and the N-terminal protecting group R² can be removed by conventional methods. For example, Cbz groups can be removed by hydrogenolysis.

Therefore, compounds 20 or 22 prepared by the method of the invention are peptide derivatives of α-aminoboronic acids, and are useful to inhibit the growth of mammalian cells, particularly cancer cells.

Each of the compounds of the invention comprise one or more, preferably one to two, amino acids coupled to an acid-terminal α-aminoboronic acid, which can optionally be linked to a boron-terminal protecting group —Y¹—Y²—, as illustrated by the foregoing formula. The nature of the B-terminal protecting group —Y¹—Y²—can vary widely within the scope of the present invention. Suitable values for —Y¹—Y²—include moieties derived from compounds, principally $C_2$–$C_{12}$ diols, having at least two hydroxy groups separated by at least two connecting atoms in a chain or ring. Contemplated compounds within the foregoing description include, for example, pinacol, perfluoropinacol, pinanediol, ethylene glycol, diethylene glycol, catechol, 1,2-cyclohexanediol, 1,3-propanediol, 2,3-butanediol, glycerol, diethanolamine and other amino alcohols, and other equivalents apparent to those skilled in the art.

Preferably, the compounds of formula I that are useful in the present invention are free boronic acids (Y¹-

=Y²=H), wherein R² is a N-terminal protecting group. The phrase "N-terminal protecting group," as used herein, refers to various amino-terminal protecting groups which can be employed in peptide synthesis. Examples of suitable groups include acyl protecting groups, for example, formyl, dansyl, acetyl (Ac), benzoyl (Bz), trifluoroacetyl, succinyl (Suc) and methoxysuccinyl (MeOSuc); aromatic urethane protecting groups, for example, benzyloxycarbonyl (Cbz); and aliphatic urethane protecting groups, for example, tert-butoxycarbonyl (Boc) or adamantyloxycarbonyl. Gross and Mienhofer, eds., *The Peptides*, Vol. 3 (Academic Press, New York 1981), pp. 3-88, disclose numerous suitable amine protecting groups.

Compounds of the invention having side-chain amino groups, for example, where $A^1$, $A^2$ or $A^3$ are Lys or Arg, can optionally comprise suitable N-terminal protecting groups attached to the side chains; similarly, amino acid residues having acidic or hydroxy side chains can be protected in the form of benzyl or other suitable esters or ethers.

Pharmaceutically acceptable salts of the compounds of formula I, 20 or 22 can be prepared by conventional methods useful to prepare amine salts, and include the nontoxic salts of inorganic and organic acids, e.g., the hydrochloride, sulfate, methosulfate, tartrate, succinate, hydrobromide, and phosphate salts and the like.

Figure 6:
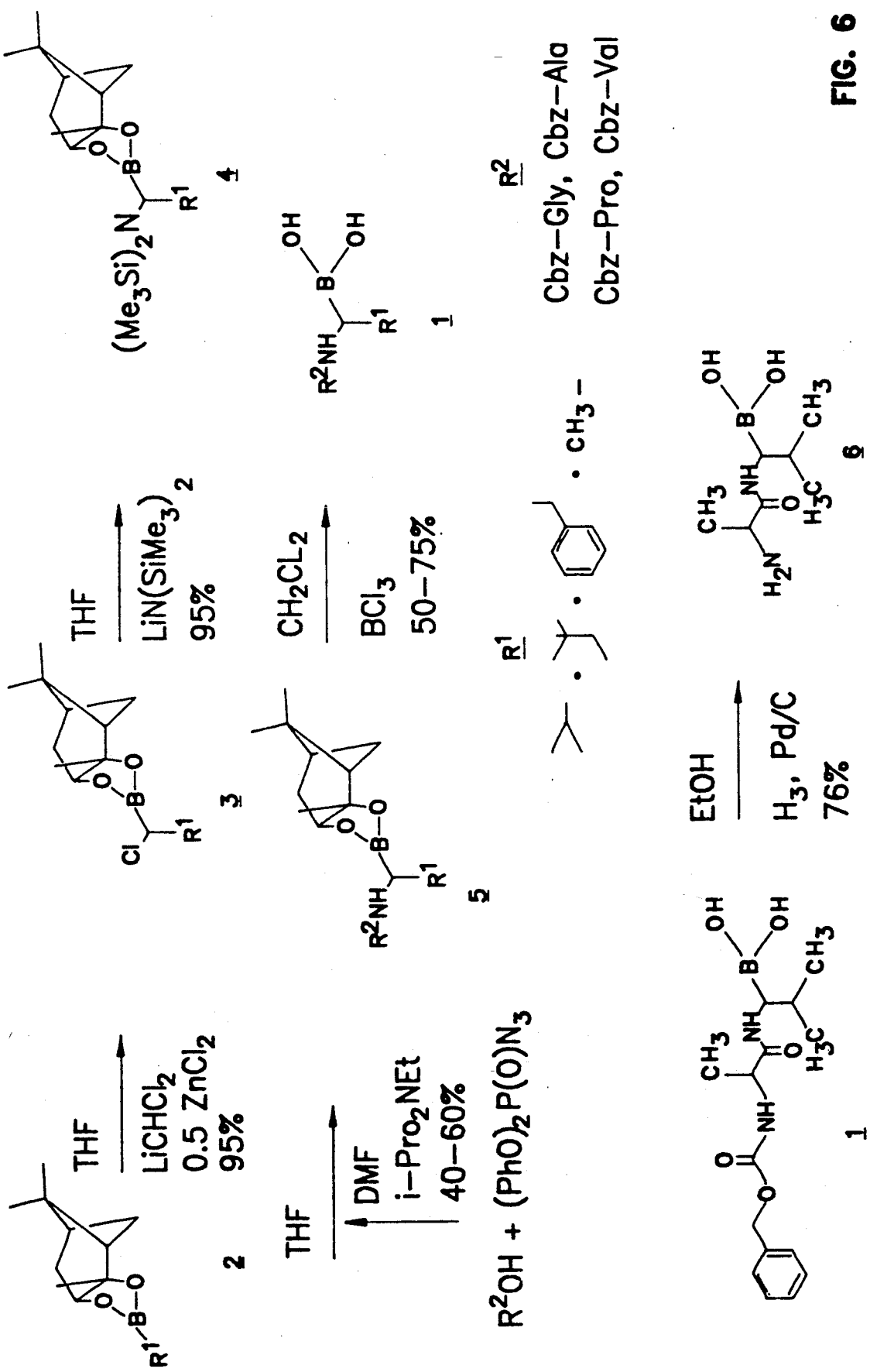
FIG. 6 illustrates the synthetic Scheme I for production of a dipeptide analog 1.

One preferred synthetic pathway for the preparation of dipeptide analogs is shown in FIG. 6. The boroamino acid analogs 1 are preferably prepared in a stereospecific manner from (+)-α-pinanediol boronic esters 2. The stereochemistry of the intermediate chloroboronic esters 3 and 1-(bis-trimethylsilyl)aminoboronic esters 4 has been previously isclosed (see Matteson, *J. Amer. Chem. Soc.*, 103, 5241 (1981)).

Utilizing the method of this invention, a wide variety of amino acids can be coupled to pinanediol aminoboronic esters, thereby forming compounds of the type 5 in yields of from about 40% to about 60%.

Cbz-protected amino acid acyl azides are generated in situ from N-protected amino acids ($R^2OH$) using diphenylphosphoryl azide in the presence of a non-nucleophilic amine, preferably di-isopropyl ethyl amine (i-Pro₂NEt) followed by tetrabutyl ammonium fluoride-dihydrofluoride (n-Bu₄NF.2HF). The 1-(bis-trimethylsilyl)aminoboronic esters 4 are added to Cbz-protected amino acid acyl azides to remove the trimethylsilyl groups in dimethyl formaldehyde/tetrahydrofuran (DMF/THF) solvent mixtures. The non-nucleophilic amine, i-Pro₂NEt, is used as base in place of triethylamine (Et₃N) (a usual base in peptide coupling reactions) to minimize proteodeboronation facilitated by trimethylammonium salts as observed in previous reactions. (See, for example, D. H. Kinder, *J. Med. Chem.*, 28, 1917 (1985)).

The boronate esters, such as the pinanediol esters can be cleaved with about 3 mole equivalents for $BCl_3$ in $CH_2Cl_2$ at approximately 0° C. to yield the free boronic acids (1). The ester cleavage or hydrolysis is in contrast to previously published methods which rely upon destruction of a pinanediol group to liberate the boronic acid. (See, for example, D. H. Kinder et al., cited above.) The hydrolysis reaction of this invention, however, is complete within about 5 minutes. The reaction is subsequently quenched by the addition of 1 M NaOH which prevents reformation of the starting pinanediol ester from the liberated pinanediol and aminoboronic acid.

The Cbz-deprotected dipeptide analogs can be prepared from 1 by hydrogenolysis in ethanol. The general reaction, illustrated by way of example for the compound ala-borovaline 6, is shown in FIG. 6. The analog 6 is produced in 76% yield after recrystallization from minimal volumes of water.

Fluorescent Labeled and Tripeptide Analogs

Figure 7:
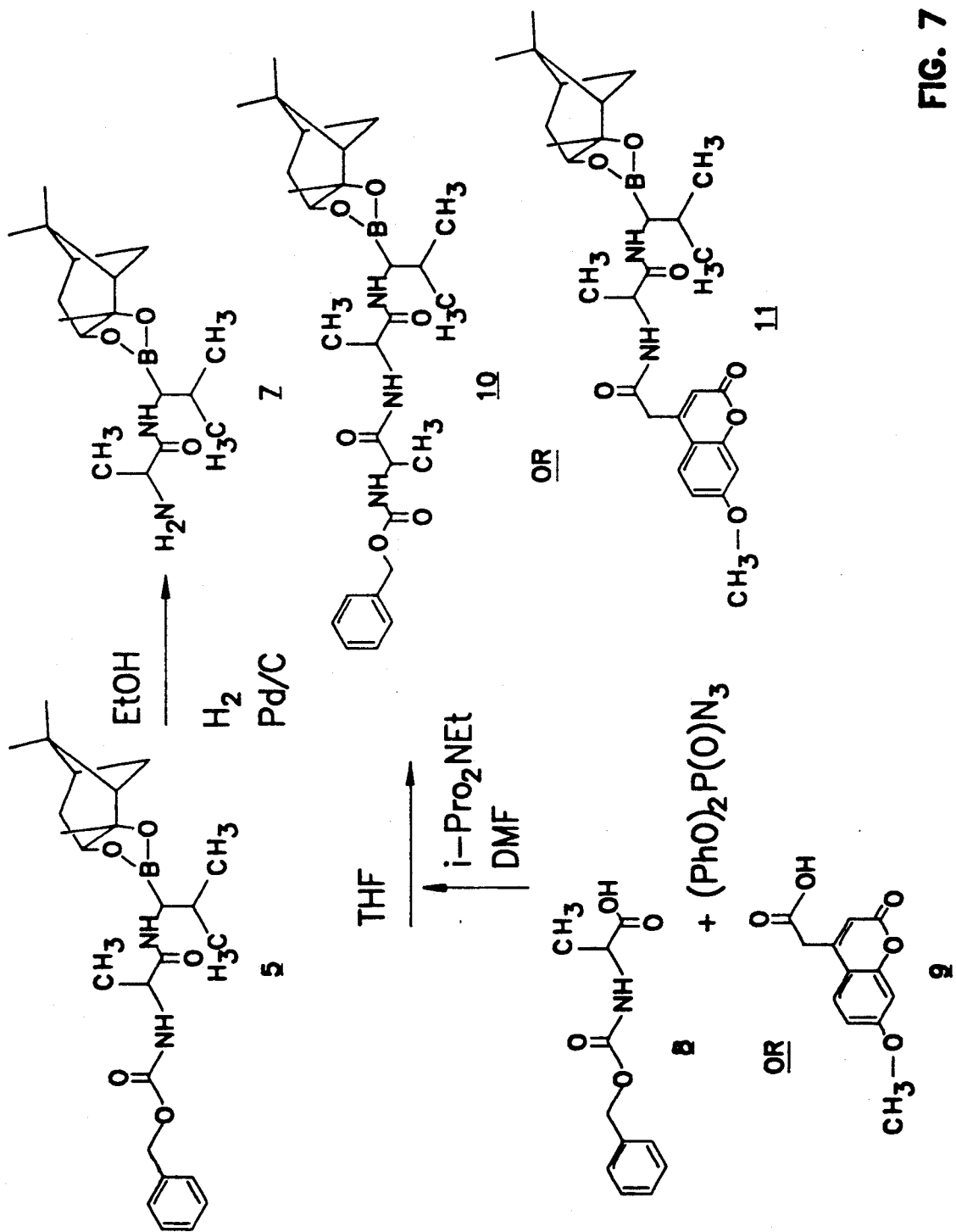
FIG. 7 illustrates the synthetic Scheme II for coupling of additional amino acid residues or other moieties to an N-terminal end of the dipeptide analogs.

7-Methoxycoumarin-4-ylacetyl analog 11, and tripeptide analog 10 can be prepared as shown for the borovaline analogs in FIG. 7. Following hydrogenolysis of the Cbz group of 5 to yield 7, a suitably N-protected amino acid (e.g., Cbz-alanine [8]) is coupled to the free amino group of 7 using the acyl azide method described above to produce tripeptide analog 10. Similarly, 7-methoxycoumarin-4-ylacetic acid (9) can be coupled to 7 to give the fluorescent dipeptide analog 11.

Removal of the pinanediol ester group can be accomplished as described above. However, in the particular case of the fluorescent analog 11, care must be taken to minimize destruction of the coumarin moiety by $BCl_3$. Specifically, the 7-methoxycoumarin-4-acetate group is converted to 7-methoxy-4-methylcoumarin by $BCl_3$ in excess of the three equivalents needed for pinanediol ester cleavage or upon extended reaction times.

The dansyl analog of the dipeptide or tripeptide analogs can be prepared similarly by reaction of the deprotected amino group with 5-dimethylamino-1-naphthalenesulfonyl chloride (dansylchloride).

Compounds That Have Been Prepared

Figure 8:
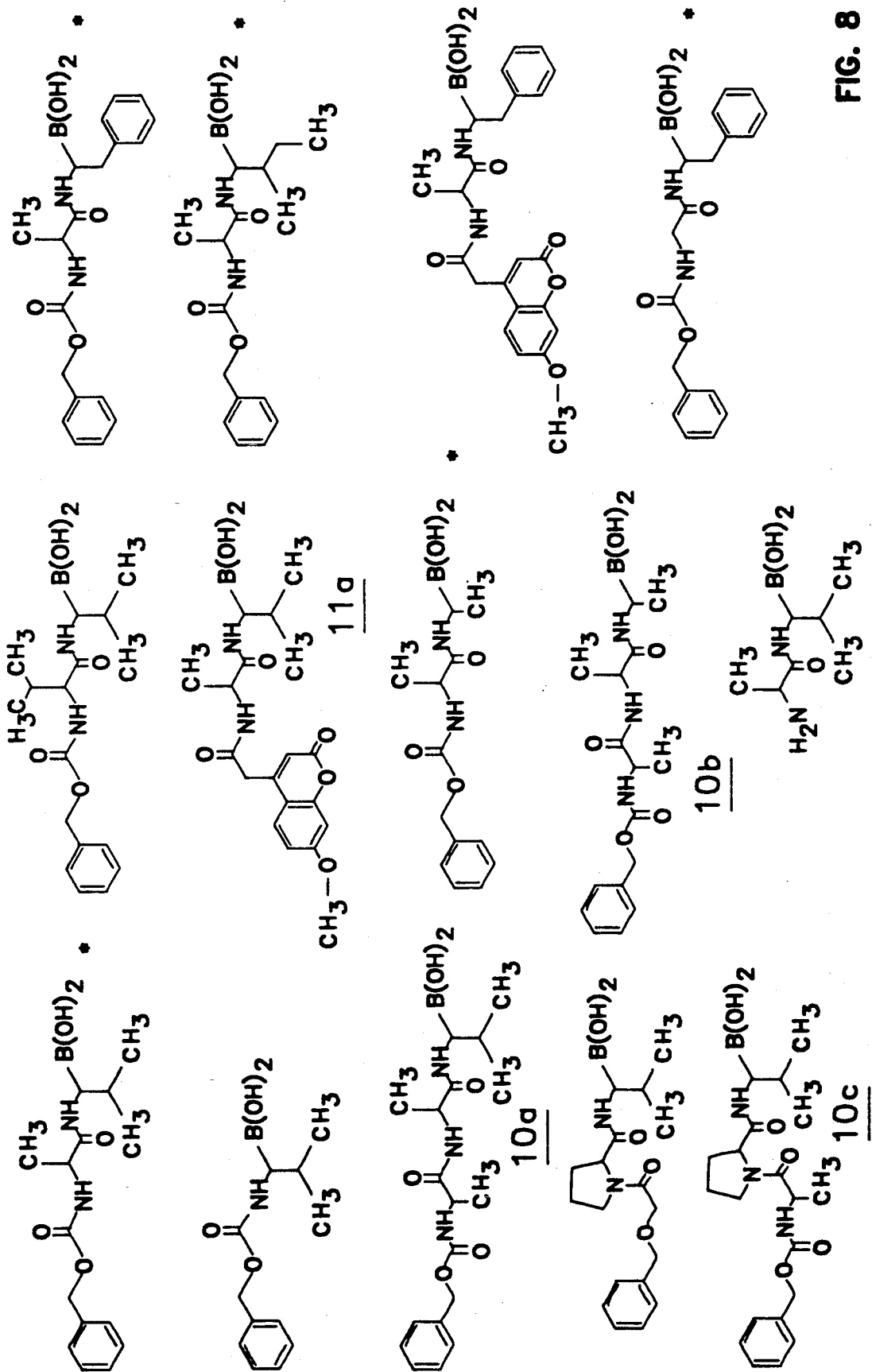
FIG. 8 illustrates boronic acid pepides which have been prepared.

FIG. 8 shows structures of molecules which have been prepared by the method of the invention. An asterisk (*) denotes previous production by Kinder et al., *J. Med. Chem.*, cited above, by a different method.

It is believed that the method of the subject invention is also useful in preparing additional compounds of the general type I. Specifically envisioned are compounds modeled on $P_1$ sites of substrates of elastase and chymotrypsin, or other proteases frequently associated with tumor cells. Generally, the compounds are of the type $R_x$—$R_1$—NH—$(P_1)CHB(OH)_2$, where $R_x$ is a hydrogen or an amino protective group or fluorescent label, and $R_1$ and $P_1$ are amino acids or peptides, independently, in either the (d) or (l) configurations. The choice of $R_1$ is preferably based on known substrate specificity. The boronic amino acid analog is in the (R) configuration which corresponds to the (l)-amino acid. The (S) configuration (e.g., (d) amino acid analog) can be established starting from (-)-α-pinanediol boronic esters as described above.

For elastase, preferred $P_1$ side chains are: isopropyl(-borovaline), 2-butyl(boroisoleucine), 2-methylpropyl(-boroleucine), methyl(boroalanine).

For α-chymotrypsin, preferred $P_1$ side chains are: benzyl(borophenylalanine), 4-hydroxybenzyl(borotyrosine), 3-$CH_2$-indole(borotyptophan).

For plasmin and plasminogen activator, preferred $P_1$ side chains are: 2-guanidinoethyl(boroarginine), 4-aminopentyl(borolysine). For other proteases, $P_1$ side chains include: 2-(methylthio-ethyl(boromethionine), $CH_2COX$ (X=OH, boroaspartate, X=$NH_2$, boroasparagine) $CH_2CH_2COX$ (X=OH, boroglutamate, X=$NH_2$, boroglutamine).

Therapeutic Applications

Methodologies and dosages useful to inhibit the growth of human cancer cells in vitro are fully set forth in the Examples hereinbelow. With respect to in vivo cancer therapy, a number of vehicles and modes of administration are available to the art which can be employed to administer one or more of the compounds of formula I to a mammal, such as a human patient, afflicted with cancer.

For example, useful liquid vehicles which may be employed for the administration of the present peptide anticancer drugs include the glycerol-ethanol solvent mixtures disclosed in U.S. patent application No. 178,139 and the buffered aqueous glycerol solvents disclosed in Canadian Patent No. 1,252,717. Other useful liquid vehicles include the aqueous triglyceride emulsions disclosed by M. M. Ames et al., in *Cancer Treatment Reports*, 66, 1579 (1982) and by R. L. Richardson in *Proc. Amer. Assoc. Cancer Res.*, 27, 166 (1986). Of course, if a given boronic acid or ester peptide is sufficiently water-soluble, it may be administered in aqueous solution, e.g., in a physiological saline solution such as phosphate-buffered saline. See Lougheed et al., *Diabetoloqia*, 19, 1 (1980).

The peptide solutions or dispersions can also be encapsulated in liposomes, and dispersions of liposomes in an appropriate liquid vehicle can be parenterally administered, as disclosed by Suzuki et al. (U.S. Pat. No. 4,016,100), Jizomoto et al. (U.S. Pat. No. 4,673,567) and by Rahman et al., *Cancer Research*, 42, 1817 (1982).

Parenteral or enteral administration of solutions or dispersions of the present peptide analogs can be employed, with intraperitoneal or intravenous injection or infusion being the preferred route. For example, a unit dosage of one or more of the present peptide analogs is dissolved or dispersed in the appropriate vehicle and infused into the bloodstream of the patient, e.g., over 0.5–18 hours, in order to achieve delivery of the desired amount of the drug in mg/kg of body weight. Although simple drip-type infusion can be employed, the use of externally or internally-placed infusion pumps permits substantially continuous infusion of the peptide, and can maintain substantially constant serum levels of the peptide. Useful infusion pumps for in vivo drug delivery are disclosed in Blackshear et al. (U.S. Pat. No. 3,731,681), and in Dorman et al. (U.S. Pat. No. 4,772,263).

Total or unit dosages effective to inhibit the growth of the cells of a particular cancer in vivo will be determined empirically, based upon the responses observed in appropriate animal models and/or in clinical trials. Due to the high stability of the present analogs, as compared to other bioactive peptides, and their low toxicity, it is anticipated that the useful serum levels of the compounds can be varied widely, as dictated by the type and stage of the cancer or cancers to be treated. For example, unit doses may vary from about 0.1–0.2 mg/kg/day to as high as 50–250 mg/kg/day per day initially, with maintenance doses administered once or twice a week thereafter.

The invention will be further described by reference to the following detailed Examples.

Bioactivity

Figure 2:
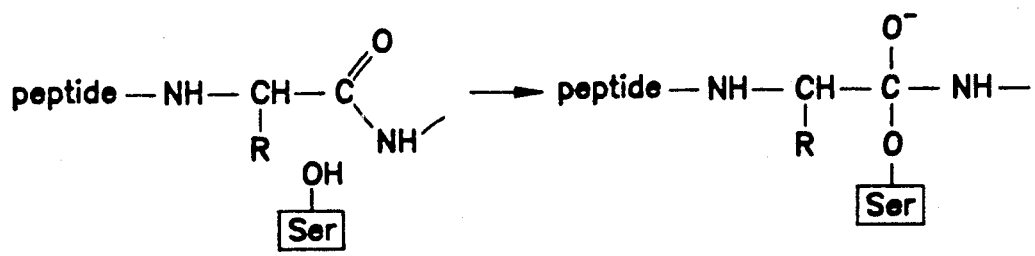
FIG. 2 illustrates serine protease mechanism (upper panel) and inhibitor mechanism (lower panel).
Figure 2:
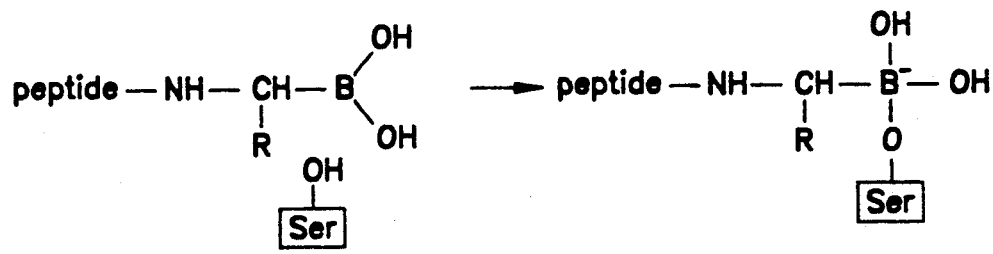

All of the molecules produced by the method of this invention are formally boronic acid analogs of dipeptides or tripeptides, although the method can be readily adapted to prepared tetra-, penta- and higher polypeptide analogs. One representative tripeptide analog of the invention has been evaluated for its ability to inhibit the replication of cancer cells. Also, a number of dipeptide analogs have been evaluated as potential anticancer agents. It is believed that the analogs can function as protease inhibitors by mimicking the transition state of serine protease-catalyzed peptide hydrolysis, as shown in FIG. 2.

Both the previously known and the new peptide analogs are inhibitors of the enzymes elastase and/or chymotrypsin (and quite possibly other proteases). Additionally, the analogs are cytotoxic to human and murine tumor cells in culture. Thus, the analogs are expected to be useful as anticancer agents.

However, in vitro data on the analogs, most particularly the tripeptide analog Cbz-ala-ala-boroalanine, (10a on FIG. 8) and the two dipeptide analogs shown in FIG. 1, have been very striking by comparison with other inhibitors. Thus far, growth inhibition and colony formation inhibition of the two dipeptide analogs against a human melanoma cell line, a human lung carcinoma cell line, and a murine leukemia cell line (L1210) have been observed. The tripeptide analog 10a inhibits the growth of human A375 melanoma cells in vitro. In addition, the analogs demonstrate a lack of inhibition of macromolecular synthesis, specifically DNA and protein synthesis.

Initial growth inhibition studies against L1210 murine leukemia cells in culture suggest that the boronic acid analogs of dipeptide compounds are very cytotoxic. Following a 72-hour exposure to 0.03 uM ala-1-borovaline, approximately 50% growth inhibition was observed. The two compounds are also cytotoxic to human tumor cell lines. While not yet fully understood, the mechanism of cytotoxicity is not via macromolecular synthesis inhibition in the human tumor cell lines.

The invention will be further described by reference to the following detailed examples. The numerals correspond to those on FIGS. 6 and 7.

EXAMPLE 1

Pinanediol Cbz-alanyl-borovaline (5, $R^1$=iPr, $R^2$=Cbz-Ala)

The bis-trimethylsilylaminoboronic ester (4) generated from the treatment of the 1-chloroboronic ester (31) with $LiN(SiMe_3)_2$ (0.1 mol) is reacted with Cbz-Ala-$N_3$ generated from Cbz-Ala, diphenylphosphorylazide and diisopropylethylamine at 0° C. in dimethylformamide (DMF), in a 1:1 mixture of DMF:tetrahydrofuran with concomitant deprotection of the amino group with tetrabutylammonium fluoride-dihydrogenfluoride, for 18 hrs (The ammonium fluoride salt provides an anhydrous source of fluoride ion for deprotections. The material is also non-acidic, being prepared by the neutralization of n-$Bu_4$NOH with 3 equivalents HF followed by drying.) The reaction mixture is diluted with ether, and the organic layer is consecutively washed with water, 1 M HCl, 10% $NaHCO_3$, water, and brine. The product is purified by flash chromatography on silica gel, using 50% ethyl acetate./hexane as eluting solvent, and is recrystallized from hexane/ethyl acetate mixtures to yield 2 6 g of 5 ($R^1$=iPr, $R^2$=Cbz-Ala) (56%); NMR: δ ($CDCl_3$, 90 mHz) 7.3 (Ar, 5H, S), 6.5 (NH, 1H, d, J=7 Hz), 5.9 (NH, 1H, d, J=7 Hz), 5.0 ($CH_2$Ar, 2H, 5) 4.2 (CHN, 1H, m), overlaps with 4.3 (CHO, 1H, d), pinanediol peaks at 2.5 (bm, 6H), 1.6, 1.2, 0.9 ($CH_3$, 9H), 1.4 (($CH_3$)$_2$CH, 6H, d, J=8 Hz), 1.6 ($CH_3$CHN, 3H, d, J=7 Hz).

EXAMPLE 2

Pinanediol Cbz-alanyl-alanyl-borovaline (10)

The dipeptide 5, $R^1 = iPr$, $R^2 = Cbz\text{-}Ala$ (250 mg) is treated with 50 mg 5% Pd/C under $N_2$ atmosphere in 10 ml absolute ethanol. Hydrogen is then bubbled through the reaction mixture, and the reaction is monitored by TLC. Upon completion of the reaction, the flask is flushed with $N_2$, and catalyst is removed by filtration through Celite. After evaporation of the solvent, the material is coupled to Cbz-Ala as described in Example 1, using the acylazide method. The reaction mixture is diluted with ether, and the organic layer separated. The aqueous layer is washed with ethyl acetate, and the organic layers are combined. The organic layer is washed with 10% bicarbonate, followed by 1 M HCl, water and brine. After drying and evaporation of solvents, the product is recrystallized from ethyl acetate/hexane mixtures. NMR:δ (CDCl$_3$) 7.3 (s, 5H), 6.7 (d, NH), 6.2 (d, NH), 5.6 (d, B—CH—NH), 4.2 (m, CHN, —CHOB), 3.8 (dd, CH—B), (pinandiol peaks as Example 1), (1.6, d, CH$_3$ 6H) 1.4 (d, (CH$_3$)$_2$CH, 6H).

EXAMPLE 3

Cbz-alanyl-alanyl-borovaline (10a).

The protected tripeptide 10 (typically 0.5-5 mmol) is added to a 0.3-0.5 M solution (five-fold excess) of BCl$_3$ in 1:2 CH$_2$Cl$_2$/dimethoxyethane (DME) prepared at $-78°$ C., and allowed to stir for 2 hrs at $0°$ C. The disappearance of starting material is followed using TLC. The reaction is quenched with water, and the resulting mixture is diluted with ethyl acetate. The aqueous layer is separated and washed with ethyl acetate. The combined organic layers are washed with 1 M NaOH (3×2 ml), and the basic extract is acidified with 6 M HCl. The product is extracted with ethyl acetate, dried, and solvent evaporated. The product is recrystallized from acetone water mixtures after trituration of the oily residue with water to give a 33% yield of 10a as white crystals. NMR δ (DMSO-d$_6$) 7.2 (Ar, 5H, 5), 5.0 (CH$_2$Ar, 2H, 5), 4.1 (CHNH, 2H, m) 3.6 (CHB, 1H, d), 1.7 (CH(CH$_3$)$_2$, 1H, m), 1.5 ((CH$_3$CH)$_2$, 6H, dd), 1.4 (CH$_3$)$_2$CH, 6H, d, J = 8 Hz), 2.5 (B(OH)$_2$, 2.5H, bs).

EXAMPLE 4

Cbz-alanyl-prolyl-borovaline (10c) was prepared in the same fashion as 10a substituting Cbz-Pro for Cbz-Ala. The second coupling step is slower because of the secondary proline nitrogen, and that step is usually allowed to proceed overnight. Physical characteristics were consistent with the assigned structure.

EXAMPLE 5

Cbz-alanyl-alanyl-boroalanine (10b) was prepared as for 10a substituting the pinanediol 1-chloroethylboronate for the chloroboronic acid 3. Product gave physical characteristics consistent with the assigned structure.

EXAMPLE 6

Dansyl-alanyl-alanyl-borovaline

Cbz-alanyl-borovaline (10a) is deprotected to the free amino compound by hydrogenolysis. 10a, 15 mg (0.04 mmol) is dissolved in ethanol, the system is flushed with nitrogen, and 2-5 mg 5% Pd/C catalyst is added. Hydrogen is bubbled through the solution for 45 min, after which the catalyst is removed by filtration through Celite. The ethanol is removed under reduced pressure, and the residue is dried in vacuo over-night. The dried residue is dissolved in 1:1 acetone/ethanol, and 11 mg dansyl chloride is added with 2-3 drops 10% NaHCO$_3$. The solution is allowed to stir overnight in the dark. The solution is diluted with ether, washed with water, and the ether is evaporated. The yellow solid is dissolved in acetone, and precipitated with water, and after recovery of the solid, the process is repeated two times. The yellow solid was isolated by filtration, dried under vacuum, and gave 6 mg (35%) of product, mp 151°-152° C.; TLC, 30% methanol/ethyl acetate, R$_f$ =0.8; NMR δ(CDCl$_3$, 90 mHz) 8.4-7.4 (Ar, 6H, m), 6.7 (NH, 1H, d), 6.15 (NH, 1H, d), 5.65 (NH, 1H, d), 4.2 (CHN, 2H, m), 3.75 (BCH, 1H, dd), 2.95 (N(CH$_3$)$_2$, 6H, s), 1.2 (CH$_3$CHN, 6H, overlapping d), 0.95 ((CH$_3$)$_2$CH, 6H, d), 1.9 ((CH$_3$)$_2$CH, 1H, m), 1.7 (B(OH)$_2$, 2H, bs).

EXAMPLE 7

Bioactivity

A Growth Inhibition Assay

Human melanoma cells (A375) were seeded at $2 \times 10^4$ cells per tissue culture dish (60×15 mm, Falcon) in Delbecco's Minimal Essential Media (DMEM) containing 10% fetal calf serum and including 1% antibiotics. Cells were allowed to attach for 48 hours prior to exposure to drugs. Cbz-ala-1-borovaline and Cbz-ala-1-borophenylalanine were dissolved in dimethyl sulfoxide (DMSO). The final DMSO concentration in media was 0.5%. Fresh media was exchanged for the media including the drug at appropriate exposure times. Cells were counted after 24, 48 or 96 hours of growth using a Coulter counter. Growth inhibition is expressed as the percent reduction of drug treated cells with respect to untreated control cells.

B. Colony Formation Assay (CFA)

Human melanoma cells (A375) were seeded at 500 cells per tissue culture dish and allowed to recover for 48 hours. The dipeptide or tripeptide and media mixture was prepared as described above using Cbz-ala-1-borovaline, Cbz-ala-1-borophenyl-alanine, 7—O—methyl-coumarin-ala-1-boroval (11a), 7—O—methyl-coumarin-ala-1-borophe (11b) and Cbz-ala-ala-1-boroval (10a). Following peptide analog exposure, fresh media were substituted for the drug and media mixture. After 7 days, colonies were stained with 0.25% Coomassie Blue and enumerated. Data are expressed as the percent of colonies present in treated plates with respect to control plates (percent survival).

C. Macromolecular Synthesis Studies

Human melanoma (A375) cells were seeded at $1 \times 10^5$ cells per tissue culture dish 48 hours prior to the addition of the peptide analog (for example, Cbz-ala-1-borovaline or Cbz-ala-1-borophenylalanine). The drug and media mixture were prepared as described above. During the last 30 minutes of drug exposure, radioactive labeled precursors were added to the media and drug mixture. Specifically, either $^3$H-thymidine (0.2 μCi/ml, to measure DNA synthesis), $^3$H-uridine (0.2 μCi/ml, to measure RNA synthesis) or $^3$H-leucine (1 μCi/ml, to measure protein synthesis) were added. Following 30 minutes at 37° C., the cells were harvested, resuspended in physiological buffered saline (PBS) and the cells counted. An aliquot of the cell suspension was then lysed (10 mM Tris, 1 mM EDTA, 0.1% SDS) and macromolecules were precipitated with ice-cold trichloroacetic acid (TCA) (20%). Following three washes with TCA, radioactivity in the resulting pellet was counted on a Beckman LS2000 Scintillation Counter. Data is expressed as the percentage of counts incorporated into $1 \times 10^6$ treated cells as compared to $1 \times 10^6$ untreated cells (percent incorporation).

D. In Vivo Tumor Model

The highly invasive and metastatic B16-(BL6) murine melanoma was selected as an in vivo model system. Experimental metastatic potential of BL6 was determined after i.v. inoculation into the tail vein of $B_6D_2F_1$ mice. Drugs which interfere with the metastatic process will impede the colonization of the lungs by the tumors.

Tumors are grown in vitro to 90-95% confluence and are harvested with EGTA. Cells are injected i.v. into the tail vein of mice at a concentration of $5 \times 10^4$ viable cells in 0.2 ml Ca and Mg tris saline solution. Mice are fed Purina rodent chow throughout the experiment. After three weeks, mice are sacrificed by cervical dislocation, lungs are removed en bloc, and preserved in Bouin's solution to facilitate visualization of the tumors. At least 24 hrs following lung removal, lung tumor colonies are enumerated with the aid of a dissection microscope. The number of tumors in the control groups and the treatment groups are then statistically compared using the Wilcoxin 2-sample test.

The drugs were formulated in 30% propylene glycol/sterile saline solution for injection. Drugs were administered 24 hrs prior to tumor injection and again 4-6 hrs post-tumor injection. Pretreatment of animals was designed to moderate any effect the protease inhibitors might have on NK cell activities. Control mice were injected with saline in the same volume as the treated mice.

E. Results

1. Inhibition of Growth/Colony Formation

As shown in Table 1, Cbz-ala-1-borovaline and Cbz-ala-1-borophenylalanine were effective inhibitors of the growth and colony formation of human melanoma (A375) cells in culture. Human melanoma (A375) cells were exposed to Cbz-ala-1-borovaline or Cbz-ala-1-borophenylalanine for 1, 24 or 96 hours. Cells were counted following 24, 48 or 96 hours of growth. Each data point represents the average of a minimum of 3 experiments. Colony formation data is from FIG. 3C.

TABLE 1

Inhibition of A375 Growth and Colony Formation

| Exposure Time (Hours) | Concentration ($\mu M$) | Growth Inhibition (%) 24 hr | 48 hr | 96 hr | Colony Formation Inhibition (%) | IC$_{50}$ ($\mu M$) | Apparent Ki ($\mu M$) |
|---|---|---|---|---|---|---|---|
| Cbz-ala-1-Borovaline | | | | | | | |
| 1 | 29.43 | 23 | 48 | 73 | 87 | | |
| 1 | 7.36 | 14 | 33 | 46 | 41 | | |
| 24 | 1.47 | 61 | 88 | 93 | 87 | | |
| 24 | .029 | 17 | 50 | 68 | 43 | | |
| 24 | .003 | 5 | 5 | 14 | 5 | (0.91) | (0.77)(E)[1] |
| 96 | .736 | 53 | 78 | 89 | — | | |
| 96 | .029 | 21 | 51 | 68 | — | | |
| Cbz-ala-1-Borophenylalanine | | | | | | | |
| 1 | 129 | 42 | 65 | 69 | — | | |
| 1 | 51.6 | 20 | 41 | 52 | 55 | | |
| 24 | .645 | 75 | 72 | 98 | 97 | (0.17) | (0.04)(C)[2] |
| 24 | .129 | 41 | 63 | 68 | 35 | | |
| 24 | .026 | 5 | 3 | 15 | 10 | | |
| 96 | .258 | 58 | 91 | 95 | — | | |
| 96 | .1239 | 38 | 68 | 75 | — | | |
| 7-O Methylcoumarin-ala-1-Borovaline (11a) | | | | | | | |
| 24 | — | — | — | — | — | 0.15 | 0.052(E) |
| 7-O-Methylcoumarin-ala-1-Borophenylalanine (11b) | | | | | | | |
| 24 | — | — | — | — | — | 0.06 | 0.006(C) |
| Cbz-ala-ala-1-Borovaline (10a) | | | | | | | |
| 24 | — | — | — | — | — | 0.05 | 0.018(C) |
| Dansyl-ala-ala-Borovaline | | | | | | | |
| 24 | — | — | — | — | — | 0.04 | 0.57(C) |

[1]Elastase
[2]Chymotrypsin

Figure 3A:
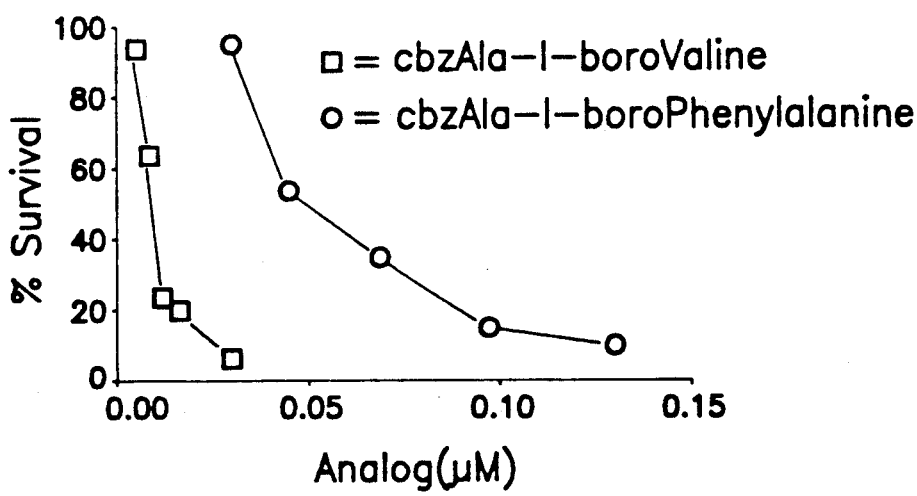
FIG. 3 illustrates colony Formation Assay. Human melanoma cells (A375) were exposed to Cbz-ala-1-borovaline or Cbz-ala-1-borophenylalanine for 1 hour (FIG. 3A), 24 hours (FIG. 3B), or continuously (169 hours) (FIG. 3C). Colonies were enumerated following 7 days of growth; each data point represents the average of 5 or more experiments.
Figure 3B:
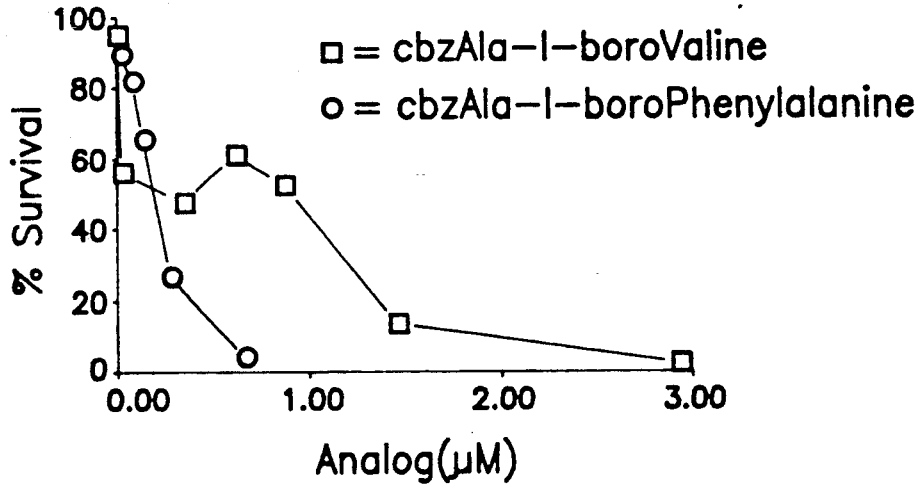
Figure 3C:
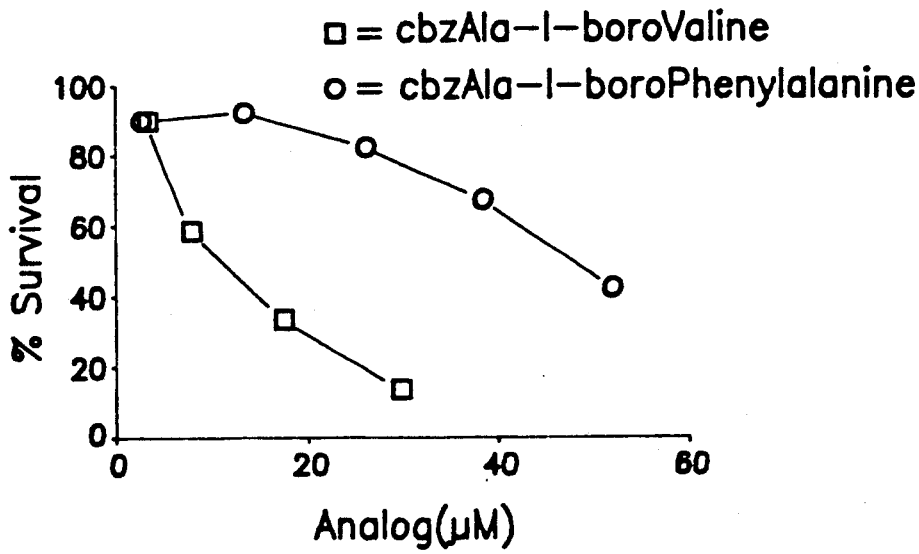

Cbz-ala-1-borovaline was a more potent inhibitor of colony formation than was Cbz-ala-1-borophenylalanine when assayed against human melanoma (A375) cells in culture (FIG. 3). Dose-dependent inhibition of colony formation was observed for both analogs. Qualitatively similar results were obtained against human lung carcinoma (A549) cells in culture (data not shown). A plateau was consistently observed with the 24-hour exposure to ala-1-borovaline between 0.029 $\mu M$ and 0.833 $\mu M$ (FIG. 3B). The plateau, however, was not observed in association with the analog after the 1-hour (FIG. 3A) or continuous (FIG. 3C) exposure times. A similar plateau was never observed with Cbz-ala-1-borophenylalanine treatment. A plateau was also seen with A549 cells.

Longer exposure times for both analogs led to enhanced inhibition of colony formation for all exposure times (FIG. 3), and enhanced inhibition of growth for the 1-hour versus 24-hour or 96-hour exposure (Table 1). The observed results are consistent with mechanisms involving schedule dependent inhibition. Such mechanisms are possibly explained as a consequence of metabolism or processing of a drug to an active species. However, no difference was observed in the growth inhibition for 24-hour versus 96-hour exposure for either Cbz-ala-1-borovaline or Cbz-ala-1-borophenylalanine (Table 1). The similarity of 24- and 96-hour exposure results on growth inhibition argues against schedule dependent inhibition.

The growth inhibition assay (Table 1) yielded qualitatively similar results as the colony formation assay.

The growth inhibitory activity of other serine protease inhibitors against human melanoma (A375) cells in culture was assessed (Table 2).

TABLE 2

Growth Inhibition Activity of Selected Protease Inhibitors
Human melanoma (A375) cells were exposed to TPCK (N-tosyl-phenylalanine chloromethyl ketone), ovomucoid or aprotinin for 96 hours. Fresh inhibitor was added every 24 hours. Data is from one representative experiment.

| TPCK | | Ovomucoid | | Aprotinin | |
|---|---|---|---|---|---|
| Conc. ($\mu M$) | % Inhib | Conc. ($\mu M$) | % Inhib | Conc. ($\mu M$) | % Inhib |
| 284 | 100 | 89.3 | 5 | 15.4 | 0 |
| 142 | 100 | 17.9 | 0 | 1.54 | 0 |
| 28.4 | 100 | 3.57 | 0 | .154 | 0 |
| 2.84 | 42 | .357 | 1 | .015 | 0 |

TABLE 2-continued

Growth Inhibition Activity of Selected Protease Inhibitors
Human melanoma (A375) cells were exposed to TPCK (N-tosyl-phenylalanine chloromethyl ketone), ovomucoid or aprotinin for 96 hours. Fresh inhibitor was added every 24 hours. Data is from one representative experiment.

| TPCK | | Ovomucoid | | Aprotinin | |
|---|---|---|---|---|---|
| Conc. ($\mu$M) | % Inhib | Conc. ($\mu$M) | % Inhib | Conc. ($\mu$M) | % Inhib |
| .284 | 9 | .036 | 0 | | |
| .028 | 5 | .004 | 0 | | |

Negligible growth inhibition was observed following treatment with the inhibitors ovomucoid and aprotinin at concentrations at which the boron analogs are potent inhibitors. Another serine protease inhibitor, N-tosyl-phenylalanine chloromethylketone (TPCK), inhibited growth at very high concentrations. However, at lower inhibition (9% inhibition at 0.284 $\mu$M) in the range, the boron analogs are very potent inhibitors (95% inhibition at 0.258 $\mu$M ala-1-borophenylalanine).

2. Inhibition of Synthesis of Macromolecules

Figure 4:
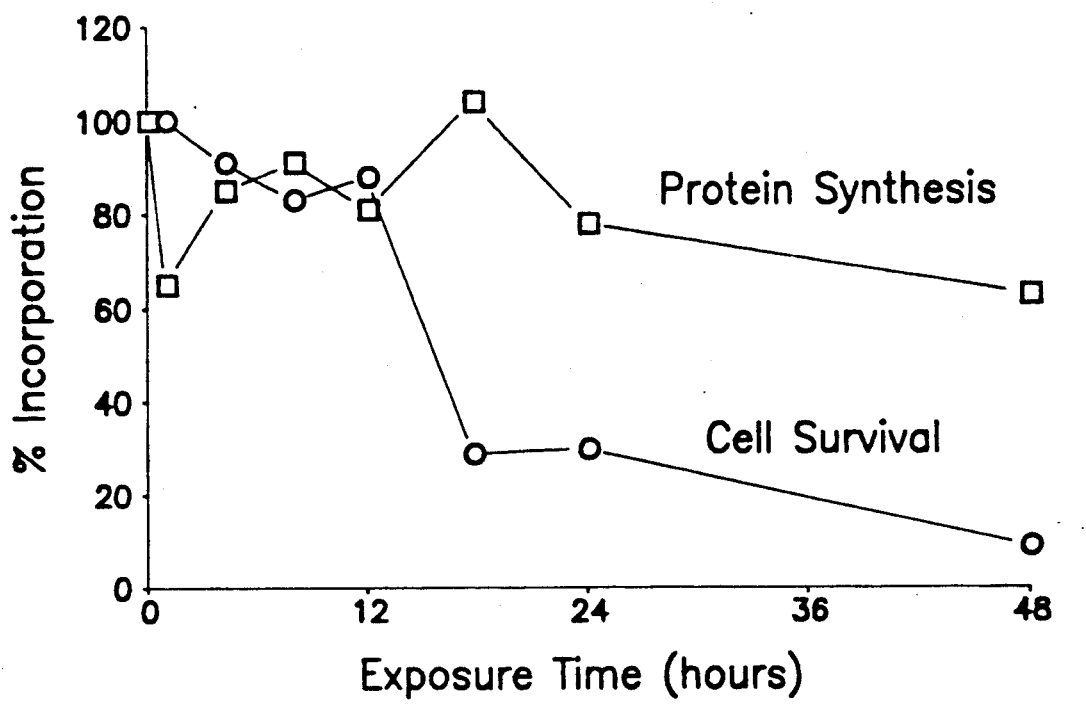
FIG. 4 illustrates inhibition of protein synthesis in A375 cells in culture by Cbz-ala-1-borophenylalanine (0.075 µg/ml). Protein synthesis was determined by the incorporation of [³H]-leucine into protein in viable cells.
Figure 5:
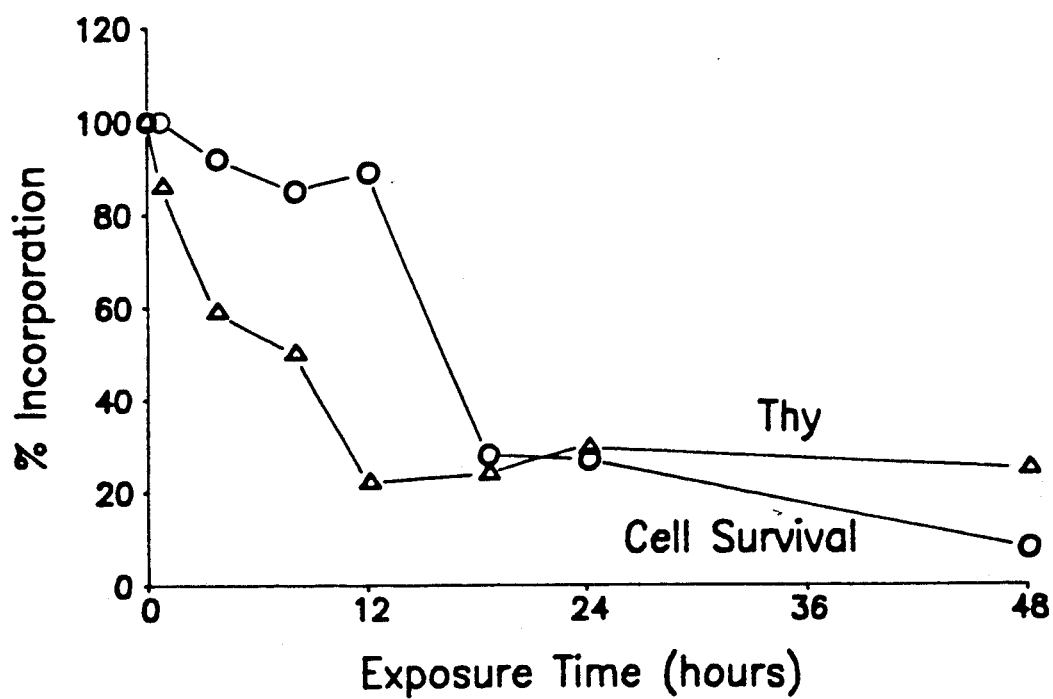
FIG. 5 illustrates inhibition of DNA synthesis in A375 cells in culture by Cbz-ala-1-borophenylalanine (0.075 µg/ml). DNA synthesis was determined by the incorporation of [³H]-thymidine into viable cells.

Cbz-ala-1-borophenylalanine did not show an acute inhibition of protein synthesis at a concentration (0.075 $\mu$g/ml) which inhibited growth by 70% after 24-hour exposure (FIG. 4). This decrease in protein synthesis follows cell survival and so most likely is a consequence of an injured cell and not a primary mechanism leading to cell death.

3. In Vivo Tumor Inhibition

Tripeptide analog Cbz-ala-ala-boroval (10a) significantly reduced the number of tumors which colonized the lung following tumor injection, as shown on Table 3, below.

TABLE 3

| Dose of 10a | Mean # Tumors | Range | Significant |
|---|---|---|---|
| Control | 31.6 | 12-77 | — |
| 1.0 mg/kg | 10.8 | 2-23 | * |
| 5.0 mg/kg | 44.3 | 19-77 | Toxicity, 6/10 |

*Denotes stastically significant at p > 0.05. (Wilcoxon two sample test).

The dipeptide analog Cbz-ala-borophe also significantly reduced the number of tumors at 0.5, 1.0 and 2.0 mg/kg.

Preliminary tests of effective boron analogs administered to mice intravenously at doses of approximately 20 mg/kg did not reveal significant toxicity or side effects.

EXAMPLE 8

Projected Phase I Studies of Boron Serine Protease Inhibitor Analogs

A. Patients and Methodology

Protease inhibitor analogs 10a, 10b, and 10c are selected for clinical evaluation based on broad antitumor activity against human tumor cells in culture and in vivo activity against murine model tumors. The Phase I clinical trial starting dose (22 mg/m$^2$) is 1/10th the LD$_{10}$ dose in mice. Patients are treated by a 15-minute intravenous infusion once every three weeks. Three new patients are evaluated at every dose. Patients with tolerable toxicity who responded or had stable disease are retreated at the same dose until disease progression. Dose escalations are determined by a modified Fibonacci scheme.

Twenty-four patients are enrolled in the three Phase I trials, three patients at the first six dose levels, and six patients at the maximally tolerated (MTD) dose of 82 mg/m$^2$. All patients are ambulatory and in a reasonable state of nutrition and have white blood cell counts greater than 4,000/mm$^2$, platelet counts greater than 130,000/m$^2$, hemoglobin greater than 10 g./dl, serum creatinine less than 1.5 mg/dl, serum alkaline phosphatase data 0, 1 or 2, SGOT levels less than 3 times normal and ECOG performance status less than 3. Patients are excluded if they present uncontrolled infection, persistent nausea and vomiting, chronic obstructive pulmonary disease, any neurological impairment, major surgery within the preceding 30 days, or radiation greater than 15% of the bone marrow within 30 days. Patients are informed of the investigational nature of this study and an informed consent is required for participation. Tests done prior to entry include a history, physical examination, tumor measurements when possible, WBC, hemoglobin, platelet count, chest x-ray, electrocardiogram, electroencephalogram, urinalysis, SGOT and serum creatinine. Of the 24 patients, two have no prior treatment, 12 have had chemotherapy only, and 10 have had chemotherapy and radiotherapy. The most common malignancies are colorectal, lung, breast, and ovarian cancer. Patients with renal, melanoma, fibrosarcoma, and hepatic cancers are also treated in these studies.

Non-hematologic toxicities observed during the trials are Grade I-II nausea and vomiting, mucositis, and mild diarrhea. Myelosuppression is the dose-limiting toxicity in this Phase I study. At higher doses, several patients exhibit platelet nadirs of approximately 50,000/mm$^2$ and white blood count nadirs 1,000–1,200/mm$^2$.

B. Compound 10a

Five of the twenty-four patients have objective evidence of antitumor activity after treatment with boron protease inhibitor analog 10a. Two patients with metastatic breast cancer with bone disease progression following previous therapy have objective evidence of tumor regression. They received five and eight cycles of treatment with the time to treatment failure of 7 months and 9+months. Two patients with recurrent small cell lung cancer have objective tumor response. Time to treatment failure in these patients is four months and seven months. The last responding patient has metastatic melanoma with cytologically confirmed metastases. The measurable breast metastases diminish in size over the next six months until they are no longer measurable. Pulmonary metastases are stable after 11+months.

C. Compound 10b

Six of the twenty-four patients have objective evidence of antitumor activity with the boron protease inhibitor analog 10b. Three patients with metastatic breast cancer with bone disease progression following previous therapy have objective evidence of tumor regression. They receive five and eight cycles of treatment with the time to treatment failure of 7 months, 8 months, and 9+ months. Two patients with recurrent small cell lung cancer exhibit objective tumor response. Time to treatment failure in these patients is four months and seven months. The last responding patient had metastatic melanoma with cytologically confirmed metastases. The measurable breast metastases diminish in size over the next six months until they are no longer measurable. Pulmonary metastases are stable after 11+ months.

D. Compound 10c.

Four of the twenty-four patients have objective evidence of antitumor activity with the boron protease inhibitor analog. Two patients with metastatic breast cancer with bone disease progression following previous therapy have objective evidence of tumor regression. They receive five and eight cycles of treatment with the time to treatment failure of 7 months and 9+months. One patient with recurrent small cell lung cancer exhibits objective tumor response. Time to treatment failure in this patient is four months. The last responding patient has metastatic melanoma with cytologically confirmed metastases. The measurable breast metastases diminish in size over the next six months until they were no longer measurable. Pulmonary metastases are stable after 11+months.

These present compounds are also useful as antiviral agents, e.g., against HIV, Herpes Simplex virus, and lentiviruses, as well as antiarthritic agents and antimalarial agents.

Although the present invention has been described with reference to preferred embodiments, workers skilled in the art will recognize that changes may be made in form and detail without departing from the spirit and scope of the invention.

What is claimed is:

1. A method of inhibiting growth of a cancer cell comprising contacting said cell with an effective growth-inhibiting amount of a compound of the formula (II):

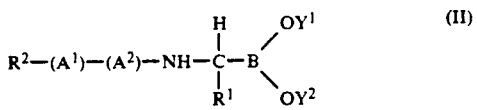

or a physiologically acceptable salt thereof, wherein A and $A_2$ are individually L-amino acid residues selected from the group consisting of Ala, Pro, Gly, Glu, Leu, Lys, Phe, Ser, Val, Ile, Arg, Tyr, Thr, Asp, Asn and Gly; $R^1$ is $C_1$–$C_6$(alkyl) which is unsubstituted or is substituted with an aromatic substituent or one or more in-chain bivalent groups selected from the group consisting of —O—, —CO—, —S—, —NH—, —CONH—, CH=CH— AND —SO$_2$—; $Y^1$ and $Y^2$ are each H, or taken together form a moiety derived from a dihydroxy compound having at least two hydroxy groups separated by at least two connecting atoms in a chain or ring, said chain or ring comprising carbon atoms, and optionally, a heteratom or heteroatoms which can be N, S or O; with the proviso that where the heteroatom is O, $R^2$ cannot be H; and $R^2$ is H or an N-terminal protecting group.

2. The method of claim 1 wherein $Y^1=Y^2=H$.

3. The method of claim 1 wherein R is benzyl, methyl, isopropyl, 2-butyl or isobutyl.

4. The method of claim 1 wherein $R^2$ is H or benzyloxycarbonyl.

5. The method of claim 1 wherein $A^2$ is Ala, Pro, Gly or Val.

6. The method of claim 1 wherein $A^1$ is Ala.

7. The method of claim 1 wherein the cancer cell is a sarcoma, melanoma, carcinoma, lymphoma or leukemia cell.

8. The method of claim 1 wherein an amount of said compound of formula II is administered to a human cancer patient which is effective to inhibit the growth of said cancer.

9. The method of claim 8 wherein said amount of said compound of formula II is administered parenterally in combination with a pharmaceutically-acceptable liquid carrier.

10. The method of claim 9 wherein said amount of said compound of formula II is administered intravenously.

* * * * *

UNITED STATES PATENT AND TRADEMARK OFFICE
CERTIFICATE OF CORRECTION

PATENT NO. : 5,106,948
DATED : April 21, 1992
INVENTOR(S) : David H. Kinder, et al.

It is certified that error appears in the above-identified patent and that said Letters Patent is hereby corrected as shown below:

Title page,
item [73] Assignee: "Mao Foundation" should read --Mayo Foundation--.

Column 3, line 50, "x=y-1," should read --x=y=1,

Column 3, line 67, "A" should read --$A^1$--

Column 5, line 14, "$K_1$" should read --$K_i$--

Column 5, line 53, "$R^{2(a1)}N_3+$" should read --$R^2(A^1)N_3+$--

Column 10, line 62, "2 6 g of 5" should read --2.6g of 5--

Column 18, line 7, "A" should read --$A^1$--

Column 18 line 25, "R" should read --$R^1$--

Signed and Sealed this

Thirtieth Day of November, 1993

Attest:

BRUCE LEHMAN

Attesting Officer

Commissioner of Patents and Trademarks